US008824626B2

(12) United States Patent
Coln et al.

(10) Patent No.: US 8,824,626 B2
(45) Date of Patent: Sep. 2, 2014

(54) REDUCED-NOISE INTEGRATOR, DETECTOR AND CT CIRCUITS

(75) Inventors: Michael Coln, Lexington, MA (US); Paraic Brannick, Raheen (IE); Colin G. Lyden, Baltimore (IE); Cathal Murphy, Duleek (IE)

(73) Assignee: Analog Devices, Inc., Norwood, MA (US)

( * ) Notice: Subject to any disclaimer, the term of this patent is extended or adjusted under 35 U.S.C. 154(b) by 0 days.

(21) Appl. No.: 13/493,775

(22) Filed: Jun. 11, 2012

(65) Prior Publication Data

US 2013/0329853 A1 Dec. 12, 2013

(51) Int. Cl.

| | |
|---|---|
| ***H05G 1/60*** | (2006.01) |
| ***G06G 7/18*** | (2006.01) |
| ***A61B 6/03*** | (2006.01) |

(52) U.S. Cl.

USPC ............... 378/19; 327/337; 327/514; 330/58; 330/59; 250/370.09

(58) Field of Classification Search

CPC .................................... H05G 1/60; H03F 3/08

USPC ................................ 378/19, 98.8; 250/370.09

See application file for complete search history.

(56) References Cited

U.S. PATENT DOCUMENTS 7,298,151 B2 11/2007 Kapusta et al.
2006/0119427 A1 * 6/2006 Roos et al. ....................... 330/86

* cited by examiner

*Primary Examiner* — Allen C. Ho
*Assistant Examiner* — Danielle Fox
(74) *Attorney, Agent, or Firm* — Kenyon & Kenyon, LLP

(57) ABSTRACT

A detector circuit can include an integrator having an amplifier, a first feedback capacitor connected between an input and output of the amplifier, one or more additional feedback capacitors connected by at least one switch between the input and output of the amplifier, and a shunt capacitor connected to the output of the amplifier. The shunt capacitor can be selected to have a capacitance value greater than that of a minimum but less than that of a maximum feedback capacitance. The detector circuit can further include a sampling circuit having a sampling capacitor connected to the output of the integrator amplifier through at least one switch, wherein the sampling capacitor is separate from the shunt capacitor. A computed tomography imaging apparatus can include the detector circuit.

23 Claims, 5 Drawing Sheets

REDUCED-NOISE INTEGRATOR, DETECTOR AND CT CIRCUITS

BACKGROUND

Low noise operation is an important goal for many circuits. In computed tomography (CT) medical imaging, for example, the noise performance of circuitry used to detect X-rays passing through a patient impacts the precision with which the X-ray dose to the patient can be kept within safe limits. In a typical CT detector circuit, an integrator is used to detect charge generated by a photodiode in response to the X-rays passing through the patient. As the integrator occupies a relatively early position in a circuit chain, its noise performance can dictate, or at least greatly influence, the overall noise performance of the CT detection circuitry.

Several drawbacks exist, however, with using previous integration circuits in noise-sensitive applications such as CT imaging, which also involve the detection and measurement of signals over a potentially large dynamic range. Noise performance is a greater concern at smaller signal magnitudes than at larger signal magnitudes in a given dynamic range. As a result, an integrator designed to provide sufficient full scale performance for larger signals may not provide sufficient performance for smaller signals. Similarly, an integrator designed to provide sufficient noise performance for smaller signals may impose undesirable disadvantages for larger signals.

Thus, a need exists for circuits, including integrators for use in CT imaging, that have improved noise performance over a high dynamic range without unacceptable accompanying drawbacks.

DETAILED DESCRIPTION

Embodiments of an integrator circuit can generate an output signal, representing an integration of a received input signal, while demonstrating improved noise performance optimized for the level of signals being processed. The integrator can include an amplifier, one or more feedback capacitors that can be selectively connected in feedback about the amplifier, and at least one selectively sized shunt capacitor connected across the output of the amplifier.

Several aspects of the integrator circuit can provide improved noise performance. At least one of the feedback capacitors can be selectively connected and disconnected in feedback about the amplifier in response to the integrated output signal level, to reduce the feedback capacitance selected at lower levels to provide optimized attenuation of input-referred noise. The shunt capacitance can also have a value selected to be between that of a minimum and maximum operational feedback capacitance, to provide a reduced noise bandwidth of the integrator circuit, in combination with a detector element, at lower signal levels.

Figure 1:
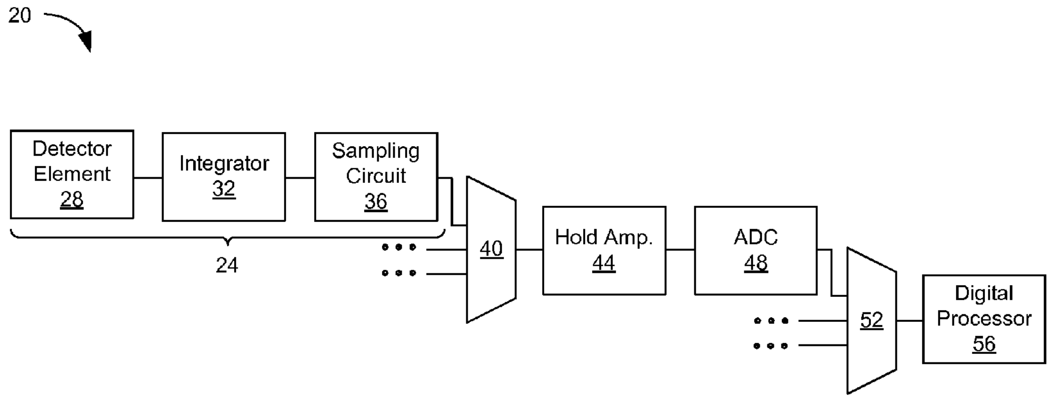
FIG. 1 is a circuit schematic depicting an embodiment of a detector circuit for a CT imaging apparatus.

FIG. 1 depicts an embodiment of a detector circuit 20 that can include the integrator circuit 32. The detector circuit 20 can be used in a CT imaging apparatus, and can include a plurality of detection channels 24. Each detection channel 24 can have a detector element 28, the integrator circuit 32, and a sampling circuit 36.

The detector element 28 can include a photodiode to detect radiation produced in response to X-rays passing through a test object being imaged. The integrator circuit 32 can integrate, or similarly process, a detection signal received from the detector element 28 to generate an integrated detection signal. The sampling circuit 36 can include a capacitor to sample the integrated detection signal to generate a sampled detection signal.

Embodiments of the detector circuit 20 can also include a first multiplexer 40 to multiplex a plurality of sampled detection signals from the plurality of detection channels 24, a hold amplifier 44 to buffer the first multiplexed signal, and an analog-to-digital converter (ADC) 48 to convert the buffered signal to a digital form. The circuit chain from the plurality of detection channels 24 to the ADC 48 can also be duplicated, and a second multiplexer 52 can multiplex the plurality of digital signals and a digital processor 56 further process the second multiplexed signal.

Figure 2:
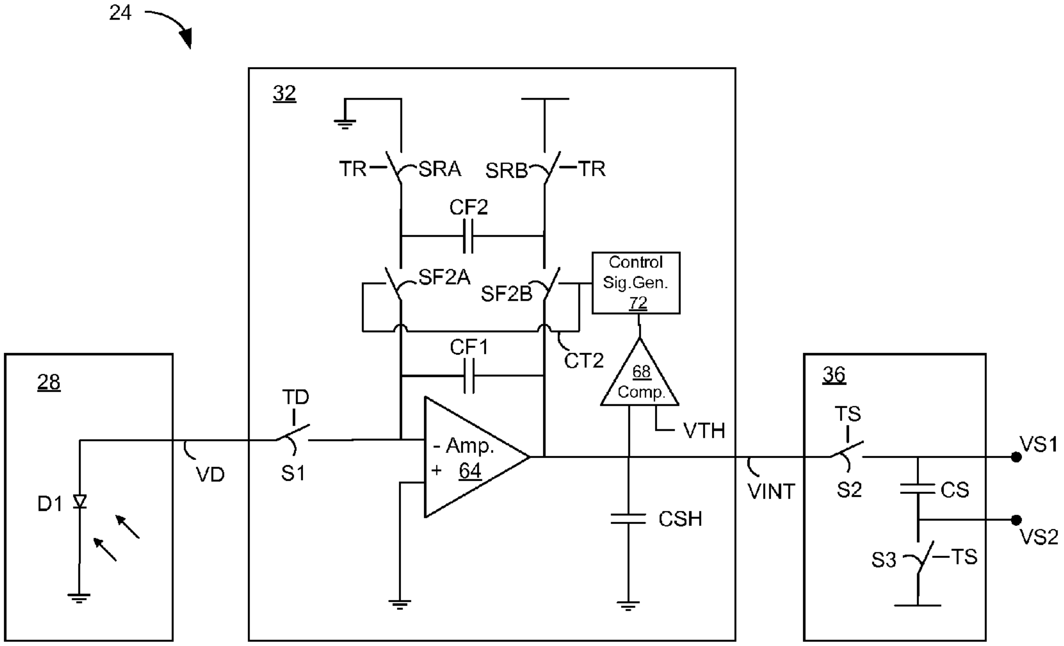
FIG. 2 is a circuit schematic depicting an embodiment of a detection channel, having a detection element, integrator circuit and sampling circuit, of the detector circuit.

FIG. 2 depicts an embodiment of the detection channel 24, showing more detail regarding embodiments of the detector element 28, integrator circuit 32, and sample circuit 36.

The integrator circuit 32 can include an amplifier 64, a first feedback capacitor CF1, a second feedback capacitor CF2, a shunt capacitor CSH, a comparator 68, a control signal generator 72, and various switches. The amplifier 64 can receive the detection signal VD from a photodiode D1 of the detection element 28 at a first input, through a switch S1, and a reference voltage, e.g., ground, at a second input. The amplifier 64 can then generate the integrated detection signal VINT at an output. The first feedback capacitor CF1 can be directly connected in feedback between the input and the output of the amplifier 64. The second feedback capacitor CF2 can be connected in parallel with the first feedback capacitor C1 by means of a pair of switches SF2A, SF2B. The shunt capacitor CSH can be connected between the output of the amplifier 64 and a reference voltage, such as a ground. A control circuit can include a comparator 68 for generating a comparison signal as a function of the received integrated detection signal VINT and a threshold voltage VTH, and a control signal generator 72 for generating a control signal CT2 for selectively electrically connecting the second feedback capacitor CF2 in feedback about the amplifier 64. One or more switches SRA, SRB can, in conjunction with other switches of the integrator 32, be used to reset voltages of the integrator 32, such as voltages at the first input and the output of the amplifier 64.

The sampling circuit 36 can include, in addition to the sample capacitor CS, a plurality of switches S2, S3, to selectively connect the sample capacitor CS to the integrator circuit 32 to sample the integrated detection signal VINT. A switch S2 can electrically connect the sample capacitor CS to the output of the integrator 32, and a switch S3 can electrically connect the sample capacitor CS to a reference voltage, such as ground, in response to a control signal TS.

Figure 3:
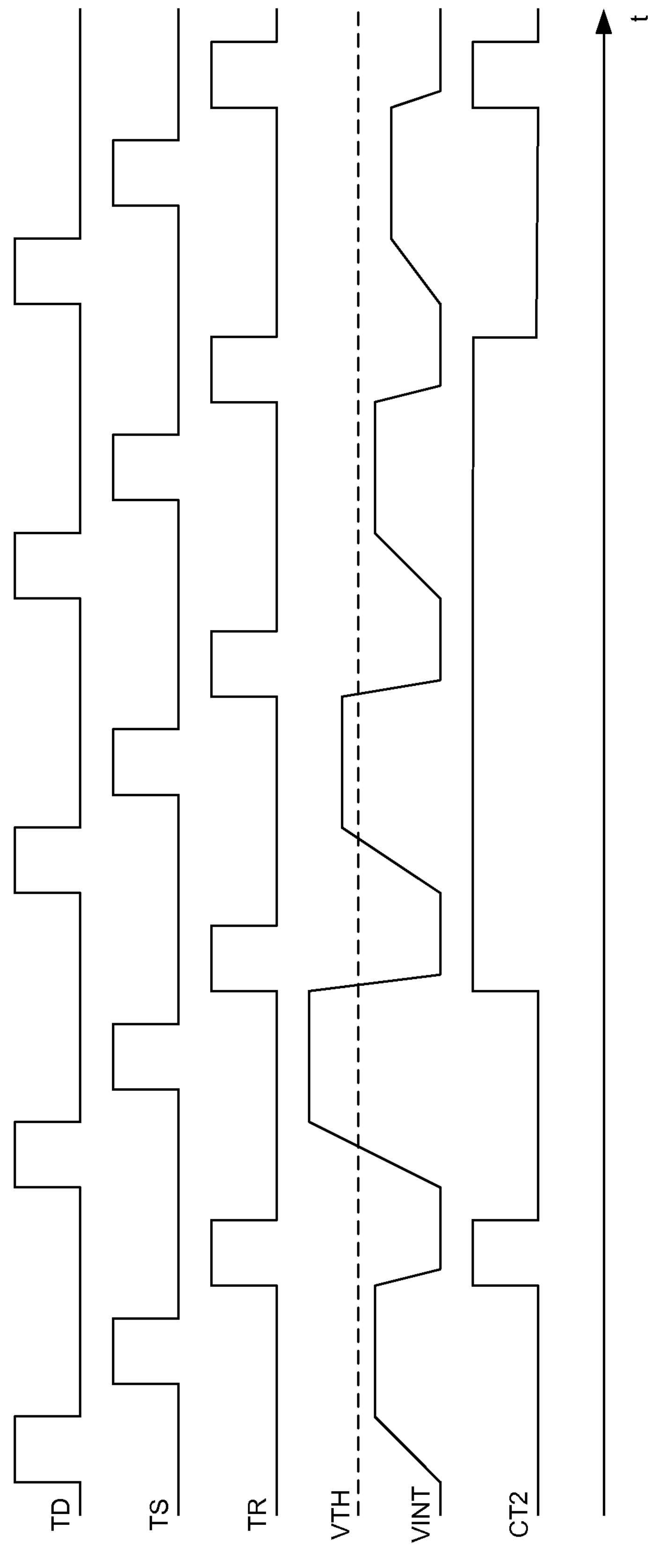
FIG. 3 is a signal diagram depicting embodiments of clocking and control signals of a multiphase clocking scheme.

Operation of the detection channel 24 of the detector circuit 20 can proceed and be controlled according to a multiphase clocking scheme. FIG. 3 depicts an embodiment of such a clocking scheme. In a first, or integration, phase, a detection clock signal TD can be activated, electrically connecting the detection element 28 to the input of the integrator 32, and marking the beginning the integration. In a second, or sampling, phase, the detection clock signal TD can be inactivated, and a sample clock signal TS activated, to electrically disconnect the detection element 28 from the integrator 32 and connect the integrator output to the sample circuit 36, ending the integration and beginning the sampling. In a third, or reset, phase, the sample clock signal TS can be inactivated, and a reset clock TR activated, enabling the reset switches SRA, SRB and interconnecting switches SF2A, SF2B, to reset voltages of the integrator 32. Note that other multiphase clocking schemes, and corresponding clocking and control signals and operational principles, are also possible.

Several aspects of the integrator circuit 32 can provide improved noise performance. First, the second feedback capacitor CF2 can be selectively electrically connected and disconnected between the input and the output of the amplifier 64 to improve noise performance by providing selectively increased attenuation of the input-referred noise at the integrator circuit 32 for relatively smaller levels of the integrated detection signal VINT.

The input-referred noise at the integrator circuit 32 can include noise generated both by the integrator 32 and by circuits succeeding the integrator 32 in a signal chain, such as the circuits succeeding the integrator 32 in the detector circuit 20 of FIG. 1. In being referred to the input of the integrator circuit 32, the noise generated by succeeding circuits is divided by the gain of the integrator 32, which can be represented as proportional to 1/CF, where CF is the total feedback capacitance connected between the first input and the output of the amplifier 64. Thus, as the input-referred noise component due to succeeding circuits is effectively multiplied by CF, from a noise perspective it may be advantageous to have as small a total feedback capacitance CF as possible to reduce the input-referred noise due to succeeding circuits as much as possible.

To implement this noise performance improvement, in response to relatively smaller signal levels of the integrated detection signal VINT, e.g., those having a first predetermined relationship to the selected threshold voltage VTH, the second feedback capacitor CF2 can be electrically disconnected from the feedback. To accomplish this, the control signal generator 72 can generate and deliver a value of the control signal CT2 to disable the switches SF2A, SF2B in response to the output of the comparator 68 generated when the integrated detection signal VINT has a level or levels having the first predetermined relationship to threshold voltage VTH. The first predetermined relationship can include, in one example, the integrated detection signal VINT having a peak signal level, during the integration phase, above the threshold voltage VTH, or, in another example, the integrated detection signal VINT having a peak signal level, during the integration phase, below the threshold voltage VTH, depending on the polarity of the integrated detection signal VINT. The total feedback capacitance CF can thus be reduced in comparison to when the second feedback capacitance CF2 is included in the feedback, and by the principles discussed above, the input-referred noise of the integrator 32 attributable to succeeding circuits can be correspondingly reduced at these relatively smaller levels of the integrated detection signal VINT. Such noise reduction can be especially important or desirable at small signal levels.

By contrast, in response to relatively larger signal levels of the integrated detection signal VINT, e.g., those having a second predetermined relationship to the selected threshold voltage VTH, the second feedback capacitor CF2 can be electrically connected in feedback in parallel with the first feedback capacitor CF1. To accomplish this, the control signal generator 72 can generate a value of the control signal CT2 to enable the switches SF2A, SF2B in response to the output of the comparator 68 generated when the integrated detection signal VINT has a level or levels having the second predetermined relationship to the threshold voltage VTH. The second predetermined relationship can include, in one example, the integrated detection signal VINT having a peak signal level, during the integration phase, below the threshold voltage VTH, or, in another example, the integrated detection signal VINT having a peak signal level, during the integration phase, above the threshold voltage VTH, depending on the polarity of the integrated detection signal VINT. In this configuration, the total feedback capacitance CF can be increased in comparison to when the second feedback capacitance CF2 is not included in the feedback. Although, correspondingly, the input-referred noise component attributable to the succeeding circuits may be increased in comparison to when the second feedback capacitance CF2 is not included in the feedback, this occurs for relatively higher levels of the integrated detection signal VINT, when noise performance may not be as critical.

FIG. 3 shows an embodiment of the control signal CT2 that can be generated to deselect the second feedback capacitor CF2 in response to peak levels of the integrated detection signal VINT below the threshold voltage VTH and select the second feedback capacitor CF2 in response to peak levels of the integrated detection signal VINT above the threshold voltage VTH. In FIG. 3, the control signal CT2 can be activated, to enable selection switches SF2A, SF2B, for the beginning of a succeeding integration phase after the integration signal VINT peaks above the threshold VTH during a given integration phase. Likewise, the control signal CT2 can be deactivated for the beginning of a succeeding integration phase after the integration signal VINT peaks below the threshold VTH during a given integration phase. Note also that in the embodiment of FIG. 3, the selection switches SF2A, SF2B can also be enabled during the reset phase, even for switching cycles corresponding to integration phases for which they are not enabled.

Other embodiments of the signals depicted in FIG. 3 are also possible. For example, some or all of these signals may have a polarity reversed from that depicted in FIG. 3. In one embodiment, the integrator circuit 32 can be configured to produce an integrated detection signal that integrates in a negative direction instead of in a positive direction as depicted in FIG. 3. In such an embodiment, the control signal CT2 can be generated to deselect the second feedback capacitor CF2 in response to peak levels of the integrated detection signal VINT above the threshold voltage VTH and select the second feedback capacitor CF2 in response to peak levels of the integrated detection signal VINT below the threshold voltage VTH. In more detail, the control signal CT2 can be activated, to enable selection switches SF2A, SF2B, for the beginning of a succeeding integration phase after the integration signal VINT peaks below the threshold VTH during a given integration phase. Likewise, the control signal CT2 can be deactivated for the beginning of a succeeding integration phase after the integration signal VINT peaks above the threshold VTH during a given integration phase. As in the embodiment of FIG. 3, the selection switches SF2A, SF2B can also be enabled during the reset phase, even for switching cycles corresponding to integration phases for which they are not enabled.

Noise performance can also be improved in a second manner, through the placement and sizing of the shunt capacitor CSH in the integrator circuit 32. Placement of the shunt capacitor CSH at the output of the amplifier 64, and selection of its capacitance magnitude relative to a minimum and maximum operational feedback capacitance CF, can improve noise performance by selectively reducing the noise bandwidth of the detector element 28 and integrator circuit 32 taken together. The size of the shunt capacitance can be selected to be relatively large in comparison to a minimum total feedback capacitance $CF_{MIN}$ at smaller integrated detection signal levels, but relatively small in comparison to a maximum total feedback capacitance $CF_{MAX}$ at larger integrated detection signal levels, i.e., $CF_{MIN}<CSH<CF_{MAX}$. This can reduce the effective transconductance of the integrator circuit 32 at small signal levels, and thereby reduce the noise bandwidth of the detector element 28 and integrator circuit 32 taken together, at these relatively smaller signal levels.

Figure 4:
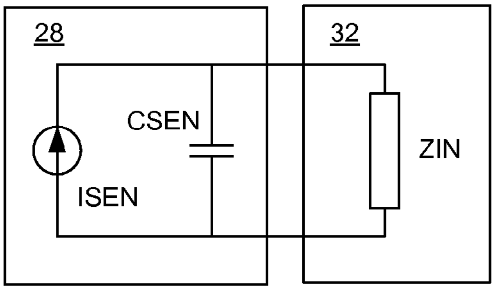
FIG. 4 is a circuit schematic depicting an embodiment of a circuit model representing the detector element and integrator circuit.

FIG. 4 depicts a circuit model representing embodiments of the integrator circuit 32 and the detector element 28, from the perspective of the input impedance presented by the integrator circuit 32 to the detector element 28. In FIG. 4, the integrator circuit 32 can be represented as an input impedance ZIN it presents to the detector element 28. The noise bandwidth of the simplified circuit of FIG. 4 can be represented as proportional to:

$$\frac{1}{ZIN \cdot CSEN}. \quad \text{(Eq. 1)}$$

The impact of the placement and sizing of the shunt capacitor CSH on the noise bandwidth of the integrator circuit 32 and detector element 28 can be explained by comparing configurations of the integrator circuit 32 and detector element 28 corresponding to both relatively smaller and larger integrated detection signal levels.

Figure 5A:
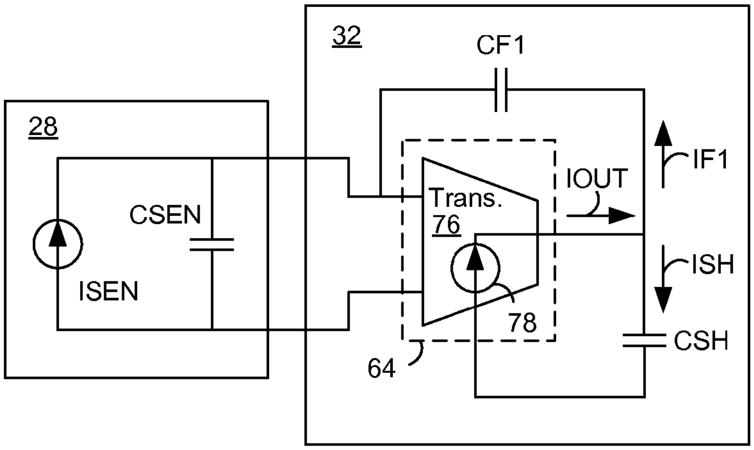
FIG. 5A is a circuit schematic depicting another embodiment of a circuit model representing the detector element and integrator circuit, in a configuration with a minimum feedback capacitance selected.

The shunt capacitor CSH can be sized to have a relatively greater impact on noise bandwidth at relatively smaller integrated detecting signal levels. FIG. 5A depicts a simplified circuit representing embodiments of the integrator circuit 32 and the detector element 28 when the integrator circuit 32 is configured to have only the first feedback capacitor CF1 electrically connected in feedback. The photodiode D1 of the detector element 28 can be represented by a current source ISEN in parallel with a capacitance CSEN. An embodiment of the amplifier 64 of the integrator circuit 32 can be represented by a transconductor 76 having a current source 78 producing an output current IOUT having a magnitude proportional to the product of the detection signal VD and a characteristic transconductance GM of the amplifier 64, or IOUT=VD·GM.

The output current IOUT can split into a first feedback current IF1 travelling into the first feedback capacitor CF1 and a shunt current ISH travelling into the shunt capacitor CSH. When the shunt capacitance CSH is selected to have a magnitude relatively larger than that of the minimum total feedback capacitance $CF_{MIN}$, or $CF_{MIN}$=CF1 in the embodiment of FIG. 2, a proportionately larger portion of the output current IOUT will generally flow into the shunt current ISH than into the first feedback current IF1. The effect of this current splitting can be to modify the input impedance ZIN, or equivalently an effective transconductance, of the integrator circuit 32, and thus also the noise bandwidth. As shown in FIG. 5A, the input impedance ZIN presented by that the integrator circuit 32 to the detector element 28 can have a value proportional to:

$$\frac{1}{GM}\frac{CF1+CSH}{CF1}. \quad \text{(Eq. 2)}$$

Without the shunt capacitor CSH present, an otherwise similar integrator circuit would present an input impedance to the detector element 28 having a value proportional to:

$$\frac{1}{GM}. \quad \text{(Eq. 3)}$$

The increased input impedance ZIN thus effected by the shunt capacitor CSH can correspondingly reduce the noise bandwidth of the combined integrator circuit 32 and detector element 28. Substituting the input impedance ZIN as expressed in Eq. 2 into the noise bandwidth formulation of Eq. 1 yields a noise bandwidth for the combined integrator circuit 32 and detector element 28 of FIG. 2, in its minimum feedback-capacitance configuration, having a value proportional to:

$$\frac{GM}{CSEN}\frac{CF1}{CF1+CSH}. \quad \text{(Eq. 4)}$$

A similar integrator circuit, but without the shunt capacitor CSH present, would yield a noise bandwidth having a value proportional to:

$$\frac{GM}{CSEN}. \quad \text{(Eq. 5)}$$

The presence of the shunt capacitor CSH can thus decrease the noise bandwidth of the combined integrator circuit 32 and detector element 28.

Note that this reduced noise bandwidth can involve an increased input impedance presented by the integrated circuit 32 to the detector element 28, as discussed above. This may not be a large concern at relatively smaller signal levels, however. Although photodiode D1 may only be guaranteed to operate within specified performance metrics with a limited range of voltages imposed across it, at relatively smaller integrated detection signal levels the detection signal can itself be smaller, and the increased voltage across the photodiode can still be relatively small and thus made to fall within acceptable limits.

Figure 5B:
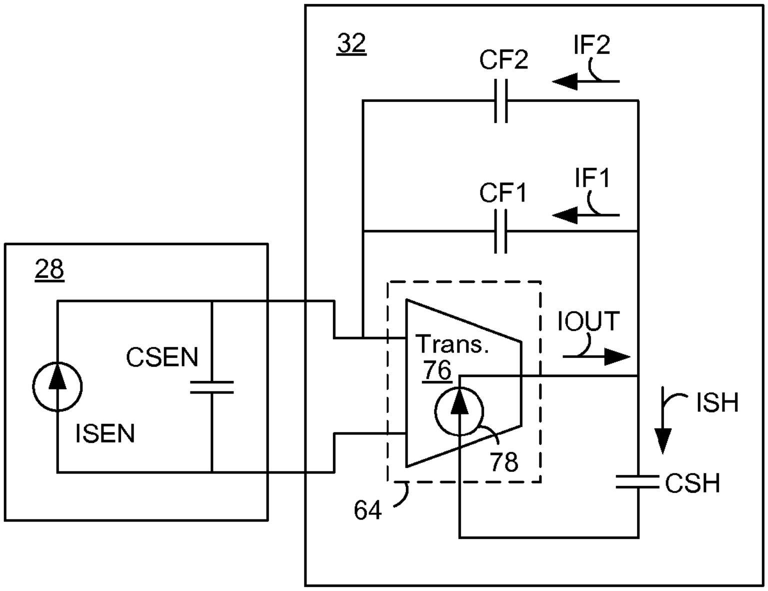
FIG. 5B is a circuit schematic depicting another embodiment of a circuit model representing the detector element and integrator circuit, in a configuration with a maximum feedback capacitance selected.

For relatively larger integrated detection signal levels, the overall effect of the presence of the shunt capacitor CSH can be less impactful. In this situation, both the first and second feedback capacitors CF1, CF2 can be connected in feedback in FIG. 2. FIG. 5B depicts a simplified circuit representing embodiments of the integrator circuit 32 and the detector element 28 in this configuration. The amplifier output current IOUT can split into three currents, a first feedback current IF1 fed back through the first feedback capacitor CF1, a second feedback current IF2 fed back through the second feedback capacitor CF2, and a shunt current ISH travelling into the shunt capacitor CSH. The input impedance ZIN that the integrator circuit 32 presents to the detector element 28*b* can have a value proportional to:

$$\frac{1}{GM}\frac{CF1+CF2+CSH}{CF1+CF2}. \quad \text{(Eq. 6)}$$

The effect of the presence of the shunt capacitor on the input impedance can thus be reduced in comparison to when only the first feedback capacitor CF1 was electrically connected in feedback. Moreover, when the shunt capacitance CSH is selected to be small relative to the maximum feedback capacitance $CF_{MAX}$, or CF1+CF2 in FIG. 2, the overall effect of the presence of the shunt capacitor CSH can be relatively small in comparison to when no shunt capacitance is present.

The noise bandwidth of the combined integrator circuit 32 and detector element 28 in FIG. 5B can be represented as proportional to:

$$\frac{GM}{CSEN}\frac{CF1+CF2}{CF1+CF2+CSH}. \quad \text{(Eq. 7)}$$

Thus, although the presence of the shunt capacitor CSH can also decrease the noise bandwidth of the combined integrator 32 and detector element 28 in comparison to the same configuration without a shunt capacitor, the decrease is relatively smaller than in the minimum feedback capacitance configuration of FIG. 5A.

For relatively larger integrated detection signal levels, the increased input impedance of the integrated circuit 32 may be more of a concern, with respect to corresponding increases in the voltage imposed across the photodiode D1, than for smaller integrated detection signal levels. For relatively larger integrated detection signal levels, the voltage appearing across the detector element 28 may already be close to the limit of an acceptable or desirable range of voltages for the photodiode D1. However, because the increase in input impedance ZIN is relatively small in this situation, this concern can be largely alleviated.

Figure 6:
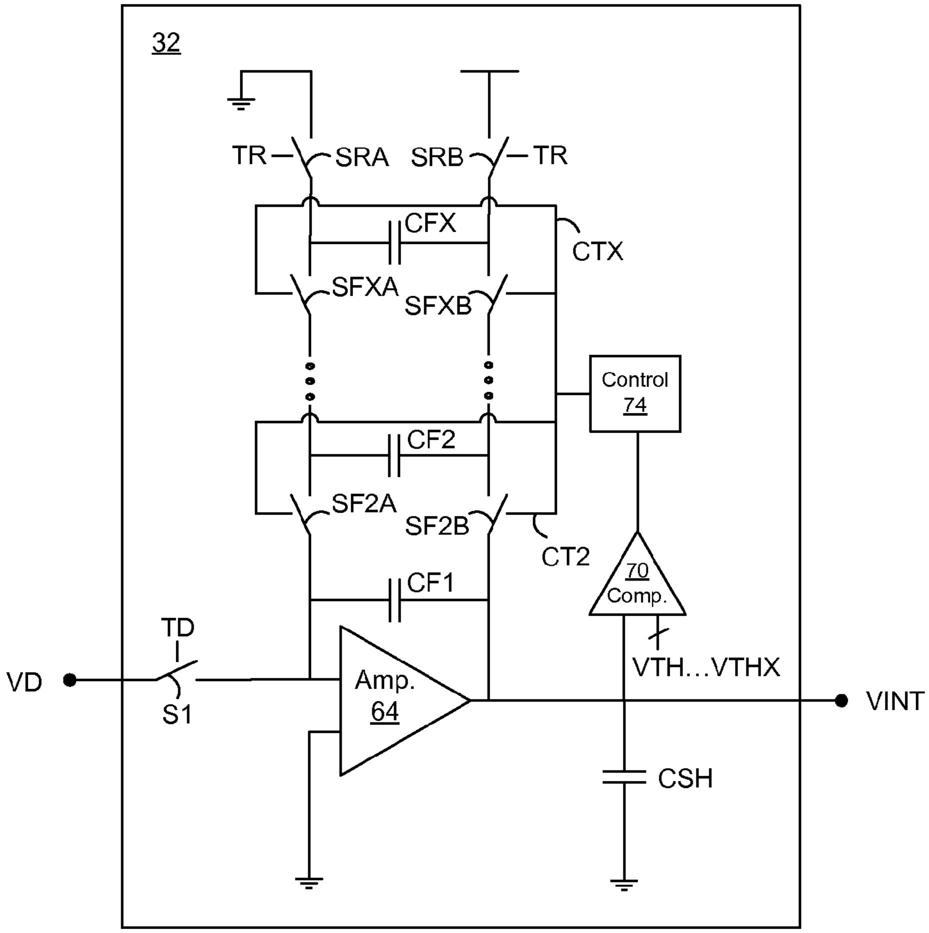
FIG. 6 is a circuit schematic depicting another embodiment of the integrator circuit.

The integrator circuit can optionally include a plurality of selectively electrically connected feedback capacitors. FIG. 6 depicts an embodiment of the integrator circuit 32 having a plurality of selectively electrically connectable feedback capacitors CF2 . . . CFX connected in parallel with the first feedback capacitor CF1 by pairs of switches SF2A, SF2B . . . SFXA, SFXB. As with the embodiment of FIG. 2, each of the plurality of selectable feedback capacitors CF2 . . . CFX can be placed into feedback by selective enabling and disabling of corresponding switch pairs SF2A, SF2B . . . SFXA, SFXB by control signals CT2 . . . CTX generated by a control signal generator 74 in response to a comparison of the integrated detection signal VINT to a plurality of threshold levels VTH . . . VTHX by a comparator 70. Embodiments of the integrator circuit 32 can optionally include any number of selectively electrically connectable feedback capacitors CF2 . . . CFX.

The plurality of selectable feedback capacitors CF2 . . . CFX can be used in an operational approach similar to that discussed above in regard to FIG. 2. A smaller number of the feedback capacitors CF2 . . . CFX can be electrically connected in feedback in response to relatively smaller levels of the integrated detection signal VINT, and a larger number of the feedback capacitors CF2 . . . CFX can be electrically connected in response to relatively larger integrated detection signal levels, but with more than two levels of operational feedback capacitance possible. Under such an approach, a more finely graded adjustment can be made than with only a single selectable feedback capacitor.

When the integrator circuit 32 includes a plurality of selectable feedback capacitors CF2 . . . CFX and a single shunt capacitor CSH, as depicted in FIG. 6, the shunt capacitor magnitude can be selected to have a value that is greater than a minimum feedback capacitance $CF_{MIN}$ but less than a maximum feedback capacitance $CF_{MAX}$ that can be connected in feedback between the first input and the output of the amplifier 64. For example, in FIG. 6, the shunt capacitance CSH can be selected to have a value greater than that of the first feedback capacitor CF1, i.e., $CF_{MIN}$=CF1, but less than that of the sum of the fixed CF1 and each of the selectable feedback capacitors CF2 . . . CFX, i.e., $CF_{MAX}$=CF1+CF2 . . . +CFX.

Embodiments of the integrator circuit can optionally include a plurality of selectable feedback capacitors instead of one fixed and one or more selectable feedback capacitors. Similarly, embodiments of the integrator circuit 32 can optionally include one or more selectable shunt capacitors instead of or in addition to one fixed shunt capacitor.

Additional switches, fuses, registers, logic, or various combinations thereof can also be utilized in place of or in addition to one or more of the switches SF2A, SF2B . . . SFXA, SFXB selecting feedback capacitors CF2 . . . CFX in embodiments of the integrator circuit 32, to provide greater flexibility in adjusting the integrator's operational characteristics.

Figure 7:
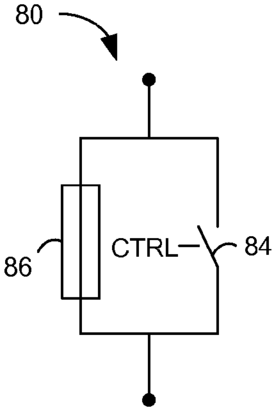
FIG. 7 is a circuit schematic depicting embodiments of a selector circuit that can be used in place of feedback- and shunt-capacitor selection switches in the integrator circuit.

For example, FIG. 7 depicts an embodiment of a selector circuit 80, having a switch 84 and a fuse element 86 connected in parallel, that can be utilized in place of one or more of the switches SF2A, SF2B . . . SFXA, SFXB in FIGS. 2 and 6. The fuse element 86 can include one or more of an electrical fuse, an electrical anti-fuse, a laser fuse, or a laser anti-fuse. The fuse element 86 can assume a first state, presenting an open circuit between its terminals, with the switch 84 of the selector circuit 80 thereby operating in much the same way as a corresponding switch that the selector circuit 80 replaces. The fuse element 86 can also assume a second state, providing an electrical short between its terminals, in which case the selector circuit 80 can operate to temporarily or permanent select the corresponding capacitor in the integrator circuit 32 regardless of the state of the selector circuit switch 84.

The selector circuit 80 can be used to provide flexibility in adjusting the operational characteristics of the integrator circuit 32. When used in place of one or more of the switches SF2A, SF2B . . . SFXA, SFXB in the embodiment of FIG. 6, for example, the selector circuit 80 can be used to temporarily or permanently select certain minimum and maximum feedback capacitances $CF_{MIN}$, $CF_{MAX}$ from a pool of available feedback capacitances CF1 . . . CFX, by a manufacture or user of the integrator circuit 32, by placing certain of the fuse elements 86 in the electrically shorting state, then leaving further selection of feedback and shunt capacitances as operational decisions by placing other fuse elements 86 in an electrically open state. In an exemplary embodiment based on FIG. 6, an available pool of feedback capacitances CF1 . . . CFX may include five such capacitances CF1, CF2, CF3, CF4, CF5, with switches SF2A, SF2B . . . SFXA, SFXB replaced by selector circuits 80. Illustratively, a manufacturer or user can optionally place fuses of the selector circuits 80 between, e.g., the first and second feedback capacitors CF1, CF2 into a temporary or permanently closed state, to select the minimum feedback capacitances $CF_{MIN}$ to have a value equal to the sum of the first and second feedback capacitances CF1, CF2. The manufacturer or user could also optionally place fuses of the selector circuits 80 between, e.g., the third, fourth and fifth feedback capacitors CF3, CF4, CF5 into a temporary or permanently closed state, to select the maximum feedback capacitance $CF_{MAX}$ to have a value equal to the sum of the first through fifth feedback capacitances CF1 . . . CF5. Fuses of selector circuits 80 between the second and third feedback capacitors CF2, CF3 could be left in an open state. In this manner, such an embodiment based on FIG. 6 can effectively be converted to a circuit similar to FIG. 2, with selection of the minimum and maximum feedback capacitances $CF_{MIN}$, $CF_{MAX}$ accomplished by selectively combining the available pool of feedback capacitances CF1 . . . CFX.

The selector circuit 80, additional switches, fuses, registers, logic, or combinations thereof can also optionally be inserted between or otherwise connected in association with each selectable feedback capacitor CF2 . . . CFX and the corresponding set of selection switches SF2A, SF2B . . . SFXA, SFXB to enable removal or addition of certain feedback capacitors from a pool of available feedback capacitors CF1 . . . CFX. This technique can be used instead of or in combination with substitution of selector circuits 80 for selection switches SF2A, SF2B . . . SFXA, SFXB.

Generally speaking, the integrator circuit 32 can also optionally include further switches, including connecting one or more of the feedback or shunt capacitances to other circuit nodes in the integrator circuit 32, for reasons of switched-capacitor circuit operation principles, such as to accommodate discrete time and clocking requirements.

The comparator 68 can operate in a variety of ways to generate the comparison signal representing the comparison between the integrated detection signal VINT and the selected threshold VTH. In one embodiment, the comparator 68 can generate the comparison signal as a function of a comparison between the instantaneous value of the integrated detection signal VINT and the threshold voltage VTH. In other embodiments, the comparator can generate the comparison signal as a function of a comparison of the threshold voltage VTH to a processed or computed measure, such as a time-average, peak-to-peak, or other characteristic, of, based on, or related to the integrated detection signal VINT.

The detector element 28 can optionally include a scintillator to transform X-rays to electromagnetic radiation of different wavelengths, capable of being detected by photodiodes.

Generally speaking, the sample capacitor CS can perform a separate function, that of sampling the integrated detection signal VINT, than does the shunt capacitor CSH, which can actively divert current, and thereby provide the improved noise performance discussed above, during integration by the integrator circuit 32. In this regard, in FIGS. 2 and 6, the shunt capacitor CSH can be continuously connected to the output of the amplifier 64 during the integration phase, whereas the sample capacitor CS can be disconnected from the integrator output during this phase using switch S2.

Figure 8:
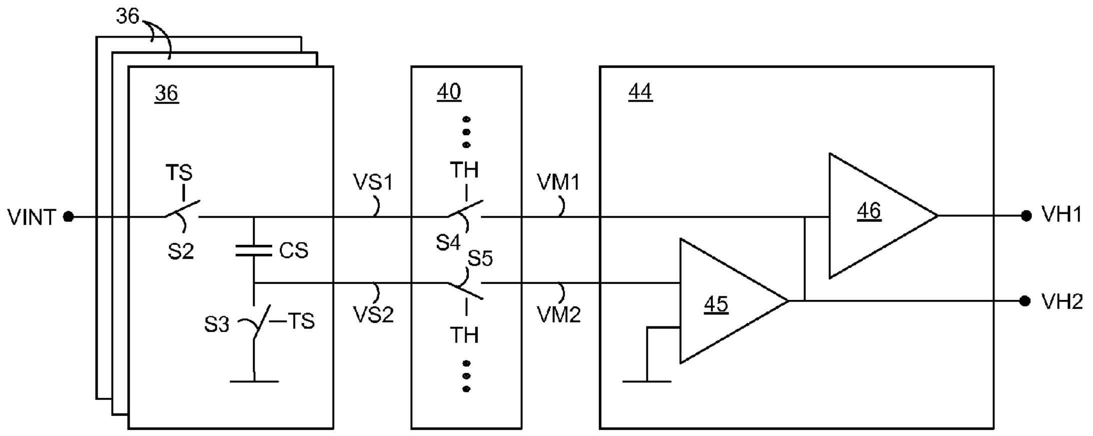
FIG. 8 is a circuit schematic depicting embodiments of the sampling circuit, a multiplexer and a hold amplifier of the detector circuit.

FIG. 8 depicts exemplary embodiments of the sampling circuit 36, first multiplexer 40, and hold amplifier 44. The first multiplexer 40 can include a plurality of switches S4, S5, two of which are shown, to receive the sampled detection signals VS1, VS2 from the sampling circuits 36 of the plurality of detection channels 24, and provide the multiplexed sampled detection signal to the hold amplifier 44. The hold amplifier 44 can include a pair of amplifiers 45, 46, having non-inverting and inverting unity gains, respectively, to buffer each end of a differential multiplexed sampled detection signal VM1, VM2 for provision to the ADC 48.

Figure 9:
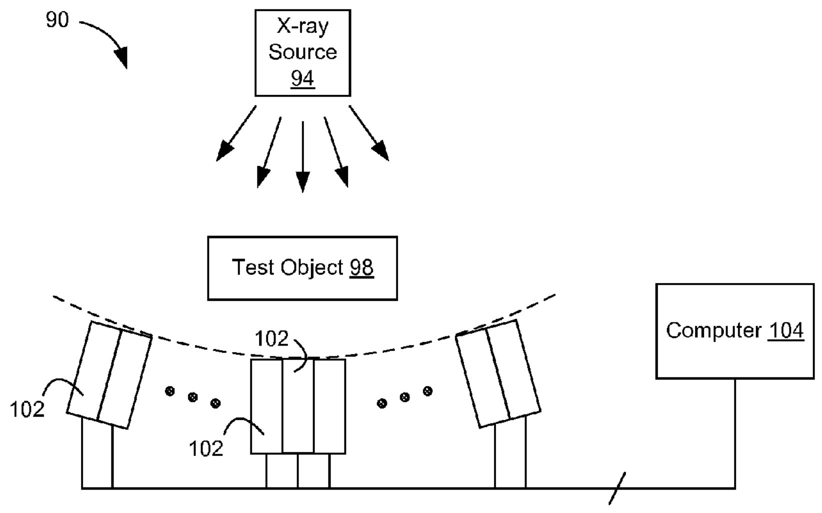
FIG. 9 is a schematic depiction of an embodiment of the CT imaging apparatus.

A CT imaging apparatus can include embodiments of the detector circuit 20 of FIG. 1. FIG. 9 depicts an exemplary embodiment of such a CT imaging apparatus 90. The CT imaging apparatus 90 can include an X-ray source 94, a plurality of detector modules 102 and a computer 104. The X-ray source 94 can produce X-rays in a direction toward a test object 98 and the detector modules 102. The detector modules 102 can each convert arriving X-rays into electrical detection signals, which can be transmitted to the computer 104 for further processing. The computer 104 can convert the electrical detection signals into two- and three-dimensional digital images for display to a user. Embodiments of the detector circuit 20 can be included as either wholly part of each of the detector module 102, or as part of the combination of the detector modules 102 and the computer 104.

Embodiments of the integrator circuit 32 can optionally utilize other signals instead of or in addition to the integrated detection signal VINT as the basis for making decisions to select feedback capacitances. For example, the comparator 68 can instead receive the threshold voltage VTH and another signal instead of the integrated detection signal VINT, such as the detection signal VD or another signal from some other node in the integrator circuit 32 or elsewhere in the detector circuit 20, and produce an comparison signal, for delivery to the control signal generator 72, as a result of a comparison between the threshold voltage VTH and such other signal. The control signal generator can then generate control signals, for enabling and disabling switches to select feedback or shunt capacitances, responsive to the comparison signal so generated. In such embodiments, the threshold voltage VTH can be selected to have a value suitable for comparison to anticipated levels of the utilized signal. In yet other embodiments, the comparison, for generation of the control signal CT2, can instead be accomplished in the digital realm by comparing one of the generated digital signals in the detector circuit 20, such as the output of ADC 48, with a digital threshold. An output of such a comparison can be delivered to an embodiment the control signal generator 72 for generation of the control signal CT2 therefrom.

In embodiments of the integrator circuit 32 such as those depicted in FIGS. 2 and 6, selection of the magnitude of the shunt capacitance CSH to be greater than the minimum operational feedback capacitance $CF_{MIN}$ but less than the maximum operational feedback capacitance $CF_{MAX}$ can be implemented in various ways, with corresponding resultant benefits. In one embodiment, the magnitude of the shunt capacitance CSH can be selected to have any value greater than the minimum operational feedback capacitance $CF_{MIN}$ but less than the maximum operational feedback capacitance $CF_{MAX}$. In another embodiment, the magnitude of the shunt capacitance CSH can be selected to have any value greater than 150% of the minimum operational feedback capacitance $CF_{MIN}$ but less than 50% of the maximum operational feedback capacitance $CF_{MAX}$. The table below lists several exemplary feedback and shunt capacitance values for embodiments according to FIG. 2:

| CF1 | CF2 | CSH |
|---|---|---|
| 0.25 pF | 2 pF | 1 pF |
| 0.5 pF | 10 pF | 2 pF |
| 1 pF | 11 pF | 3.4 pF |

Figure 10:
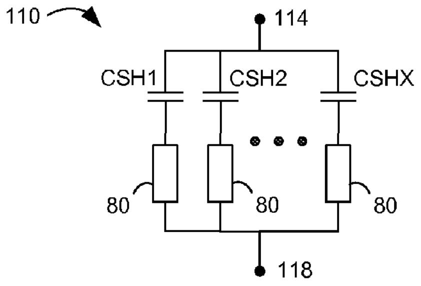
FIG. 10 is a circuit schematic depicting an embodiment of a capacitor array that can be used to implement a shunt capacitance of the integrator circuit.

Switches, fuses, registers, other logic, selector circuits 80, or combinations thereof can be used to select the magnitude of the shunt capacitance CSH. FIG. 10 depicts an embodiment of a capacitor array 110 that can be used to implement the shunt capacitance CSH of FIGS. 2 and 6. In FIG. 10, the array 110 can include a plurality of selectable capacitors CSH1 . . . CSHX arranged in parallel, via a plurality of selector circuits 80, between terminals 114, 118 representing the terminals of the shunt capacitance CSH in FIGS. 2 and 6. The value of the shunt capacitance CSH can be temporarily or permanently selected, by a manufacturer or user of the detector circuit 20, by temporarily or permanently selectively placing the selector circuits 80 into shorted or open states, to electrically connect only capacitors corresponding to the shorted selector circuits between the array terminals 114, 118. The temporary or permanent placement of selector circuits 80 into open or shorted states can be accomplished by, e.g., selectively blowing or not blowing fuses, or delivering control signals to enable or disable switches, of the selector circuits 80. The control signals delivered to switches of the selector circuits 80 can be generated in response to data, e.g., stored in a register, indicating which switches, and thus which selector circuits 80 are to be enabled and which corresponding capacitors CSH1 . . . CSHX are selected.

Additional embodiments of the integrator circuit 32, detector circuit 20 and CT imaging apparatus 90 are also possible. For example, any feature of any of the embodiments of the integrator circuit 32, detector circuit 20 and CT imaging apparatus 90 described herein can optionally be used in or with any other embodiment of the integrator circuit 32, detector circuit 20 and CT imaging apparatus 90. Embodiments of the integrator circuit 32, detector circuit 20 and CT imaging apparatus 90 can also optionally include any subset of the components or features of any embodiments of the integrator circuit 32, detector circuit 20 and CT imaging apparatus 90 described herein.

What is claimed is:

1. A detector circuit, comprising:
- an integrator, having:
  - an amplifier;
  - a first feedback capacitor connected between an input and output of the amplifier;
  - a second feedback capacitor connected by at least one switch between the input and output of the amplifier; and
  - a shunt capacitor connected to the output of the amplifier, wherein the shunt capacitor is selected to have a capacitance value greater than that of the first feedback capacitor but less than that of the parallel combination of the first and second feedback capacitors.

2. The detector circuit of claim 1, wherein the integrator amplifier generates an output signal representing an integration of an input signal received by the amplifier, and the shunt capacitor receives a current from the amplifier during the integration of the input signal.

3. The detector circuit of claim 1, wherein the integrator further comprises a control circuit to selectively enable the at least one switch to electrically connect the second feedback capacitor in feedback between the input and output of the amplifier as a function of at least one of: an output signal generated by the amplifier, or an input signal delivered to the amplifier.

4. The detector circuit of claim 3, wherein the integrator further comprises a comparator to generate a comparison signal representing a comparison between the output signal generated by the amplifier and a threshold voltage, and wherein the control circuit selectively enables the at least one switch in response to the comparison signal.

5. The detector circuit of claim 4, wherein the integrator further comprises a plurality of feedback capacitors, each connected by at least one corresponding switch between the input and output of the amplifier, and the shunt capacitor is selected to have a capacitance value greater than that of the first feedback capacitor but less than that of the parallel combination of the first and the plurality of selectively connected feedback capacitors.

6. The detector circuit of claim 5, wherein the integrator comprises a selector circuit for each of the plurality of selectable feedback capacitors, each selector circuit including the switch corresponding to the associated selectable feedback capacitor and a fuse element.

7. The detector circuit of claim 6, wherein the fuse element includes at least one of: an electrical fuse, an electrical anti-fuse, a laser fuse, or a laser anti-fuse.

8. The detector circuit of claim 5, wherein the control circuit selectively enables the corresponding switch to electrically connect each of the plurality of selectively connectable feedback capacitors in feedback between the input and output of the amplifier as a function of the output signal generated by the amplifier.

9. A detector circuit, comprising:
- an integrator, having:
  - an amplifier;
  - a first feedback capacitor connected between an input and output of the amplifier;
  - a second feedback capacitor connected by at least one switch between the input and output of the amplifier; and
  - a shunt capacitor connected to the output of the amplifier, wherein the shunt capacitor is selected to have a capacitance value greater than that of the first feedback capacitor but less than that of the parallel combination of the first and second feedback capacitors; and
- a sampling circuit, including a sampling capacitor connected to the output of the integrator amplifier through at least one third switch, wherein the sampling capacitor is separate from the shunt capacitor.

10. The detector circuit of claim 9, further comprising a plurality of detection channels, wherein each of the detection channels includes a photodiode to generate a detection signal in response to radiation received as a function of an X-ray passing through a test object, the integrator, and the sampling circuit.

11. The detector circuit of claim 10, further comprising:
- a first multiplexer to multiplex sampled detection signals output by the plurality of detection channels;
- a hold amplifier circuit to receive the multiplexed signal and generate a buffered detection signal;
- an analog-to-digital converter to convert the buffered detection signal to a digital detection signal;
- a second multiplexer to receive and multiplex a plurality of the digital detection signals; and
- a digital processor to receive and process the multiplexed digital detection signals.

12. A computed tomography imaging apparatus including the detector circuit of claim 11.

13. A detector circuit, comprising:

an integrator, having:

an amplifier;

a first feedback capacitor connected between an input and output of the amplifier;

a second feedback capacitor connected by at least one switch between the input and output of the amplifier; and a shunt capacitor connected to the output of the amplifier, wherein the shunt capacitor is selected to have a capacitance value at least 50% greater than that of the first feedback capacitor but at least 50% less than that of the parallel combination of the first and second feedback capacitors.

14. A computed tomography (CT) detector circuit, comprising:

a plurality of detection channels, each detection channel including:

a photodiode to generate a detection signal in response to radiation received as a function of an X-ray passing through a test object;

an integrator to generate an output signal representing an integration of the detection signal, the integrator having:

an amplifier to receive the detection signal through at least one switch;

a first feedback capacitor connected between an input and output of the amplifier;

a second feedback capacitor connected by at least one second switch between the input and output of the amplifier; and a shunt capacitor connected to the output of the amplifier, wherein the shunt capacitor is selected to have a capacitance value greater than that of the first feedback capacitor but less than that of the parallel combination of the first and second feedback capacitors; and a sampling circuit, including a sampling capacitor connected to the output of the integrator amplifier through at least one third switch, wherein the sampling capacitor is separate from the shunt capacitor.

15. The CT detector circuit of claim 14, wherein the integrator further comprises a control circuit to selectively enable the at least one switch to electrically connect the second feedback capacitor in feedback between the input and output of the amplifier as a function of at least one of: an output signal generated by the amplifier, or an input signal delivered to the amplifier.

16. The CT detector circuit of claim 15, wherein the integrator further comprises a comparator to generate a comparison signal representing a comparison between the output signal generated by the amplifier and a threshold voltage, and wherein the control circuit selectively enables the at least one switch in response to the comparison signal.

17. The CT detector circuit of claim 15, wherein the integrator further comprises a plurality of feedback capacitors, each connected by at least one corresponding switch between the input and output of the amplifier, and the shunt capacitor is selected to have a capacitance value greater than that of the first feedback capacitor but less than that of the parallel combination of the first and the plurality of selectively connected feedback capacitors.

18. The CT detector circuit of claim 17, wherein the integrator comprises a selector circuit for each of the plurality of selectable feedback capacitors, each selector circuit including the switch corresponding to the associated selectable feedback capacitor and a fuse element.

19. The CT detector circuit of claim 18, wherein the fuse element includes at least one of: an electrical fuse, an electrical anti-fuse, a laser fuse, or a laser anti-fuse.

20. The CT detector circuit of claim 17, wherein the control circuit selectively enables the corresponding switch to electrically connect each of the plurality of selectively connectable feedback capacitors in feedback between the input and output of the amplifier as a function of the output signal generated by the amplifier.

21. The CT detector circuit of claim 14, further comprising:

a first multiplexer to multiplex sampled detection signals output by the plurality of detection channels;

a hold amplifier circuit to receive the multiplexed signal and generate a buffered detection signal;

an analog-to-digital converter to convert the buffered detection signal to a digital detection signal;

a second multiplexer to receive and multiplex a plurality of the digital detection signals; and a digital processor to receive and process the multiplexed digital detection signals.

22. A CT imaging apparatus including the CT detector circuit of claim 21.

23. A computed tomography (CT) detector circuit, comprising:

a plurality of detection channels, each detection channel including:

a photodiode to generate a detection signal in response to radiation received as a function of an X-ray passing through a test object;

an integrator to generate an output signal representing an integration of the detection signal, the integrator having:

an amplifier to receive the detection signal through at least one switch;

a first feedback capacitor connected between an input and output of the amplifier;

a second feedback capacitor connected by at least one second switch between the input and output of the amplifier; and a shunt capacitor connected to the output of the amplifier, wherein the integrator shunt capacitor is selected to have a capacitance value at least 50% greater than that of the first feedback capacitor but at least 50% less than that of the parallel combination of the first and second feedback capacitors; and a sampling circuit, including a sampling capacitor connected to the output of the integrator amplifier through at least one third switch, wherein the sampling capacitor is separate from the shunt capacitor.

* * * * *